(12) United States Patent
Kim

(10) Patent No.: US 11,259,395 B2
(45) Date of Patent: Feb. 22, 2022

(54) BEAUTY CARE DEVICE USING PLASMA

(71) Applicant: AIRBIO INC., Seoul (KR)

(72) Inventor: Min Gee Kim, Seoul (KR)

(73) Assignee: AIRBIO INC.

( * ) Notice: Subject to any disclaimer, the term of this patent is extended or adjusted under 35 U.S.C. 154(b) by 366 days.

(21) Appl. No.: 16/162,620

(22) Filed: Oct. 17, 2018

(65) Prior Publication Data
US 2019/0053365 A1     Feb. 14, 2019

Related U.S. Application Data

(63) Continuation of application No. PCT/KR2016/013970, filed on Nov. 30, 2016.

(30) Foreign Application Priority Data

Apr. 18, 2016  (KR) .......................... 10-2016-0047104

(51) Int. Cl.
*H05H 1/24*     (2006.01)
*A61B 5/00*     (2006.01)
(Continued)

(52) U.S. Cl.
CPC ............. *H05H 1/2406* (2013.01); *A61B 5/00* (2013.01); *A61B 5/0077* (2013.01); *A61B 5/441* (2013.01);
(Continued)

(58) Field of Classification Search
CPC ..... A61B 5/0077; A61B 5/4848; A61B 5/441; A61B 5/00; A61B 18/042;
(Continued)

(56) References Cited

U.S. PATENT DOCUMENTS

| 8,267,884 B1 * | 9/2012 | Hicks .................. A61B 18/042 604/23 |
| 2002/0129902 A1 * | 9/2002 | Babayan ............... C23C 16/402 156/345.45 |

(Continued)

FOREIGN PATENT DOCUMENTS

| KR | 10-2013-0023588 A | 3/2013 |
| KR | 10-1444940 B1 | 9/2014 |

(Continued)

OTHER PUBLICATIONS

Korean Office Action (KR 10-2016-0047104), KIPO, dated Sep. 26, 2016.

(Continued)

*Primary Examiner* — Mallika D Fairchild
(74) *Attorney, Agent, or Firm* — Park & Associates IP Law, P.C.

(57) ABSTRACT

A beauty care or skin treatment apparatus using plasma includes: a body having a handle part on which a ground is formed; an electrode unit which is formed on one surface of the body and forms atmospheric plasma by application electric power thereto; an image input unit which is provided in the body so as to photograph an image of the skin which faces the image input unit; and a transmission unit which is configured to transmit an image signal inputted from the image input unit to a terminal connected thereto.

11 Claims, 8 Drawing Sheets

(51) Int. Cl.
*A61N 1/44* (2006.01)
*A61B 18/04* (2006.01)
*A61B 18/00* (2006.01)

(52) U.S. Cl.
CPC .......... *A61B 5/4848* (2013.01); *A61B 18/042* (2013.01); *A61N 1/44* (2013.01); *A61B 2018/0047* (2013.01)

(58) Field of Classification Search
CPC ......... A61B 2018/0047; H05H 1/2406; H05H 2001/2418; A61N 1/44; G03B 17/02
See application file for complete search history.

(56) References Cited

U.S. PATENT DOCUMENTS

2016/0193475 A1   7/2016  Srb et al.
2017/0319262 A1*  11/2017 Palero .................... A61N 1/403

FOREIGN PATENT DOCUMENTS

| KR | 10-2015-0118581 A | 10/2015 |
| KR | 10-1568380 B1 | 11/2015 |
| KR | 10-1577207 B1 | 12/2015 |

OTHER PUBLICATIONS

Korean Decision to Grant (KR 10-2016-0047104), KIPO, dated Nov. 7, 2016.
International Search Report (PCT/KR2016/013970), WIPO, dated Mar. 31, 2017.

* cited by examiner

BEAUTY CARE DEVICE USING PLASMA

REFERENCE TO RELATED APPLICATIONS

This is a continuation of International Patent Application PCT/KR2016/013970 filed on Nov. 30, 2016, which designates the United States and claims priority of Korean Patent Application No. 10-2016-0047104 filed on Apr. 18, 2016, the entire contents of which are incorporated herein by reference.

FIELD OF THE INVENTION

The present invention relates to an apparatus for generating plasma for beauty care or skin treatment.

BACKGROUND OF THE INVENTION

Plasma is a gas state in which electrons with negative charge and positively charged ions are separated at significantly high temperature. At this time, the charge separation is considerably high, but the number of positive and negative charges is the same overall, and thus, resulting in neutral electric charge as whole.

In general, the state of a substance is divided into three states, namely, solid, liquid, and gas states. Plasma is often referred to as the fourth states of matter. When energy is applied to a solid, it becomes a liquid, and then, a gas. When high energy is applied to the gas substance, the gas is separated into electrons and atomic nuclei at tens of thousands of degrees Celsius, thereby becoming a plasma state.

To create a plasma state, it is often necessary to apply an electrical method such as direct current, microwave, or electron beam to generate plasma, and then use a magnetic field to maintain this state.

Plasma has many classification criteria such as plasma density, electron temperature, degree of thermal equilibrium between species, generation methods, and application fields, but it is most basic to classify it into plasma density and electron temperature. The plasma can be divided into local thermal equilibrium (LTE) and non-local thermal equilibrium (non-LTE) by the degree of thermal equilibrium. The term "local thermal equilibrium" means that the temperatures of all of the plasma particles are in the same thermodynamic state in the localized region of the plasma.

Plasma used for research and manufacturing processes is usually one of LTE or non-LTE, and the former is commonly referred to as thermal plasma and the latter as low-temperature or cold plasma.

The present invention is directed to a method for providing a beauty care device for generating a low-temperature plasma, in particular, an atmospheric pressure plasma among the low-temperature plasma.

Atmospheric pressure plasma is mainly used for surface modification, coating, and environmental purification of materials. Recently, researches have been extended to applications in biomedical applications and biomedical applications as well.

Accordingly, the present invention is directed to a beauty care device which is harmless to the human body while using atmospheric plasma, and which can be portable and can identify or verify the effect of skin improvement upon use.

SUMMARY OF THE INVENTION

It is an object of the present invention to provide a beauty care or skin treatment device using plasma, with a more improved structure and having a complex function.

Another object of the present invention is to provide a beauty care or skin treatment device that can always check/identify the skin condition while using the beauty care device.

In order to solve the problems of the conventional art, the present invention provides, according to one aspect thereof, a plasma beauty/skin care apparatus which comprises: a body having a ground formed on a handle thereof; and an electrode unit provided on a surface of the body for forming an atmospheric plasma by application electric power thereto, an image input unit provided in the body to capture an image of a skin by the image input unit, and a transmission unit configured to transmit a video signal input from the image input unit to a terminal connected thereto.

According to one embodiment of the present invention, the electrode unit includes: first to third films laminated; a first conductor disposed between the first and second films and a second conductor disposed between the second and third films, so as to generate a dielectric barrier discharge therewith.

According to another embodiment of the present invention, the electrode unit includes: first and second films laminated; a first conductor and a second conductor spaced apart from each other and disposed between the first and second films so as to generate a dielectric barrier discharge therewith.

According to another embodiment of the present invention, the electrode unit includes a first dielectric member in a plate shape, a second dielectric member stacked on the first dielectric member, and a conductive electrode disposed between the first and second dielectric members so as to generate a dielectric barrier discharge thereby.

According to another embodiment of the present invention, the electrode unit includes a first conductive unit in the form of a wire, a second conductive unit surrounding the first conductive unit and twisted to form a plurality of turns, and an insulation coating layer formed on at least one of the first and second conductive units, so as to generate a dielectric barrier discharge thereby.

According to an embodiment of the present invention, first and second grounds are provided on both sides of the handle or the body, and the electrode unit can be detachably mounted on a mounting portion recessed from one surface of the body.

According to one example of the present invention, either one of the conductors, the conductive parts, or the dielectric members may be electrically connected to one of the grounds.

According to one example of the present invention, the image input unit includes: a camera configured to capture an image of the skin facing through a hole formed on a surface of the body; and a light emitting unit provided adjacent to the camera.

According to one example of the present invention, the transmitting unit may include a wireless communication module.

According to one example of the present invention, the first conductor and the second conductor are spaced apart from each other so as not to be laminated when projected on one surface thereof, and at least one of the first and second conductors is divided into at least three conductive lines.

According to one example of the present invention, an elastic body can be provided between the electrode unit and the mounting portion so that radicals generated by vibrating the electrode unit during discharge are discharged to the surroundings.

According to the present invention having the above-described structures, the skin care or treatment apparatus using the plasmas has an effect of improving the density of the skin or dermis by an antioxidant action, thereby improving wrinkles and skin elasticity. It also improves the tone of the skin and increases the permeability of the skin remedy agent into the dermis and skin. Also, by using the beauty care device, the sterilizing effect can be improved and the cleanness of the skin can be maintained.

Further, it is possible to more easily check and confirm the skin improvement state through the camera attached to the beauty care device.

DETAILED DESCRIPTION OF THE INVENTION

Figure 1:
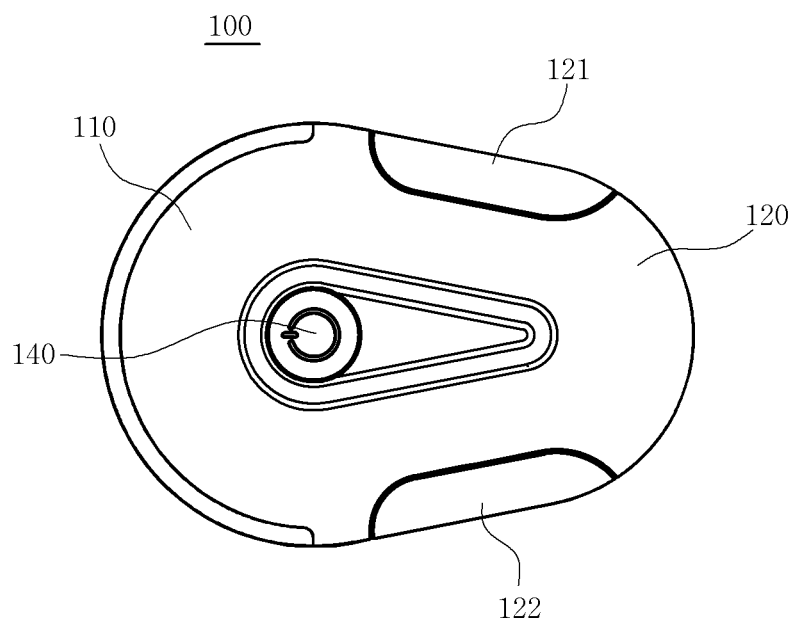
FIG. 1 is a plan view of a beauty care device using plasma, according to a first embodiment of the present invention.

Hereinafter, a beauty care apparatus using plasma according to the present invention will be described in detail with reference to the drawings. The suffix terms "module" and "part" used for constituent elements in the following description are given or used in consideration of ease of description, and do not have separate meanings or roles of their own. In this specification, the same or similar reference numerals are given to different embodiments in the same or similar configurations, and the description thereof is provided with the first description thereof. As used herein, the singular forms "a", "an" and "the" include plural referents unless the context clearly dictates otherwise.

Figure 2:
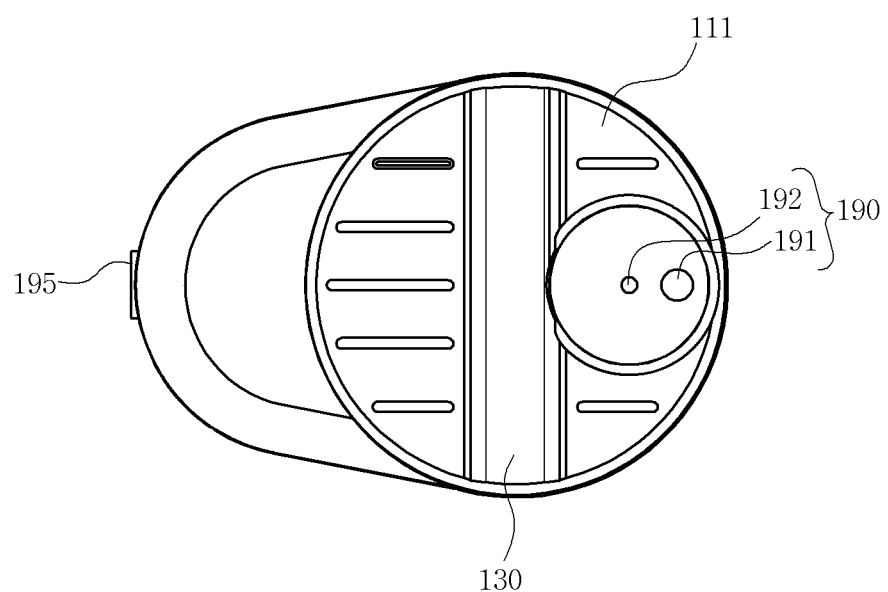
FIG. 2 is a bottom view of a beauty care device using plasma, according to the embodiment of the present invention as shown in FIG. 1.

FIG. 1 is a plan view of a plasma beauty care device according to one embodiment of the present invention;

FIG. 2 is a bottom view of the beauty care device using plasma according to the embodiment of the present invention.

Figure 3:
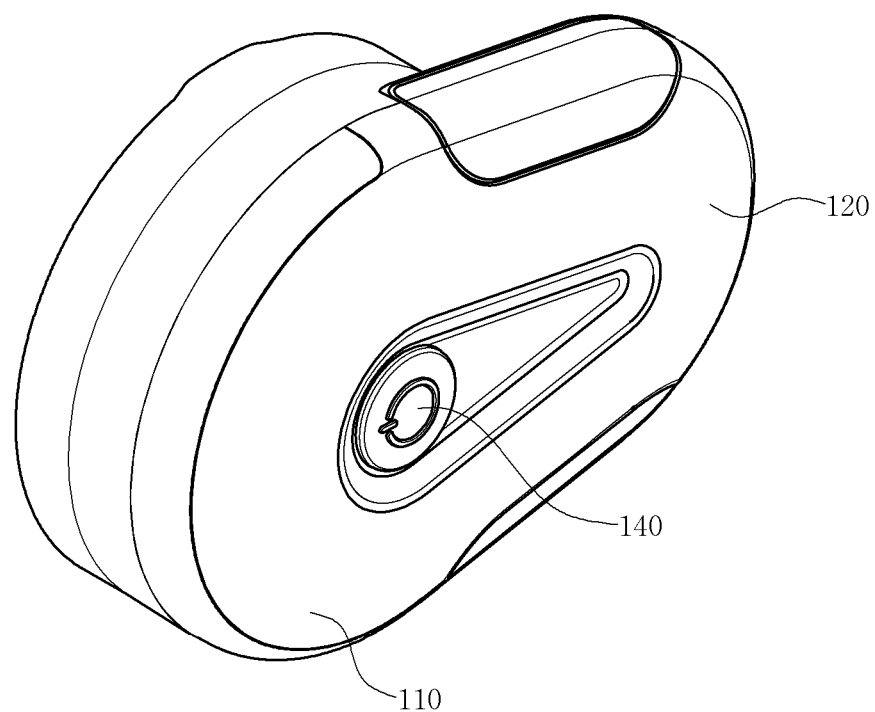
FIG. 3 is a perspective view of the beauty care device using plasma, according to the embodiment of FIG. 1.
Figure 4:
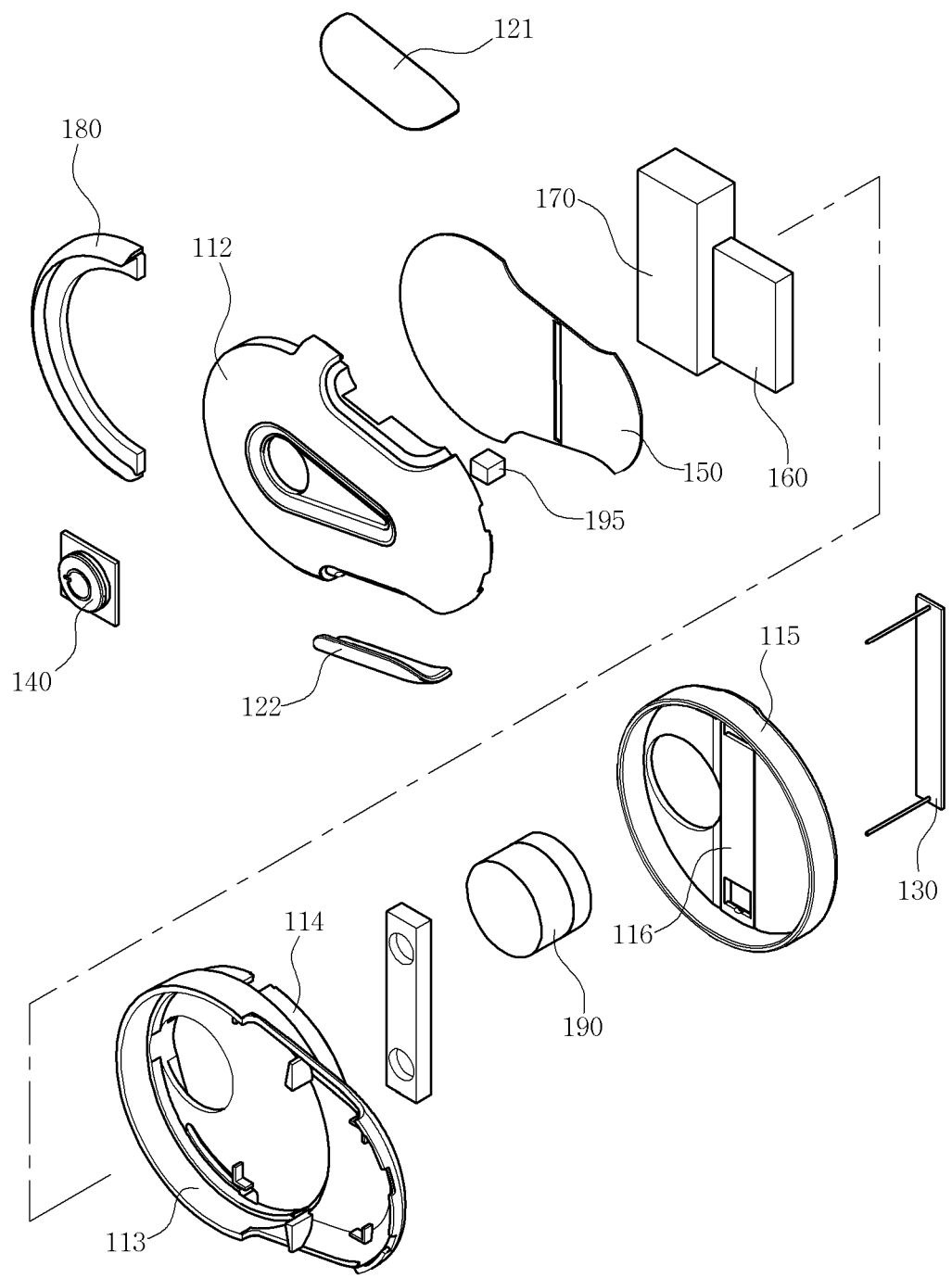
FIG. 4 is an exploded perspective view of the beauty care device using plasma shown in FIG. 1.
Figure 5:
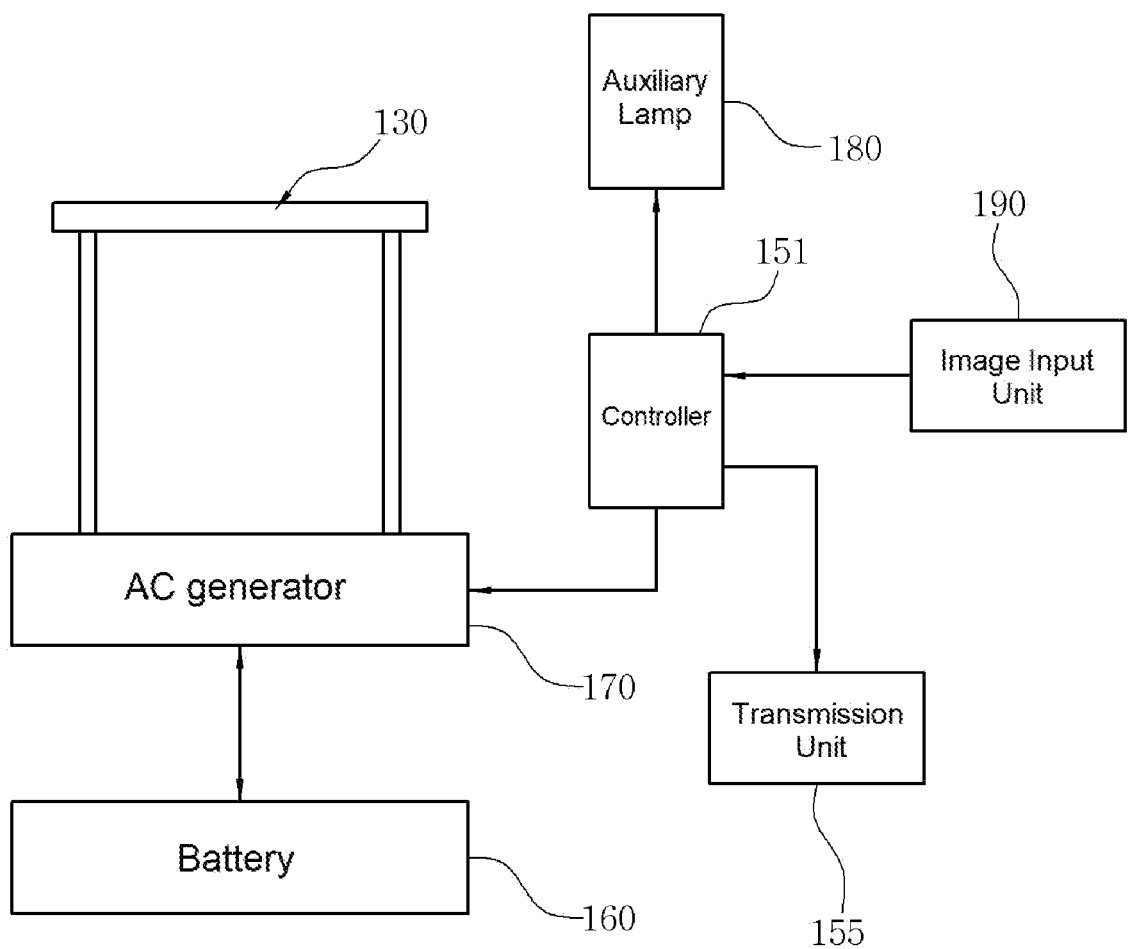
FIG. 5 is a block diagram of the beauty care device using the plasma of FIG. 1.

FIG. 3 is a perspective view of the beauty care device using plasma according to the embodiment of the present invention;

FIG. 4 is an exploded perspective view of the plasma beauty care device shown in FIG. 1;

FIG. 5 is a block diagram of the plasma beauty care device of FIG. 1.

Referring to FIG. 1 to FIG. 5, the beauty care device 100 includes body 110, 120 and electrode 130.

Referring to FIG. 1, bodies 110 and 120 constitute the outer appearance of the device 100, and are formed in a bar or similar shape so that the user can grip the device easily. Operation unit 140 is provided on the upper surfaces of the bodies 110 and 120, and grounds 121 and 122 are provided on both sides of the bodies 110 and 120. The operation unit 140 on the upper surface is used to receive a command for controlling the operation of the beauty care apparatus 100, and may include a plurality of input keys. The input keys can be employed in any manner as long as the user can operate in a tactile or similar manner. For example, a dome switch or touch screen capable of receiving a command or information by a push or touch operation of a user, a touch pad, a wheel for rotating a key, a jog method, or a joystick can be used.

The grounds are provided on both sides of the bodies 110 and 120, respectively. A first ground 121 is formed on one side of the bodies 110 and 120 and a second ground 122 on the other side of the bodies 110 and 120. Each of the grounds 121 and 122 may be electrically connected to the electrode unit 130 via a circuit board 150 or may be directly connected to the electrode unit 130.

Referring to FIG. 2, the electrode unit 130 is exposed on the rear surface of the body 110, 120.

In addition, a spacing portion may be formed along the electrode unit 130 to leave a suitable space between the electrode unit 130 and the skin. The body 110 and 120 can be divided into an upper/left portion 110 and a lower/right portion 120, and the electrode unit 130 and the operation unit 140 are formed on the upper portion 110 and the lower portion 120, respectively. The lower portion 120 corresponds to a grip portion formed to be gripped by a user, and the grounds 121 and 122 may be formed on the grip portion.

The image input unit 190 may be formed on one side of the body. For example, the image input unit 190 can be formed on the front, back, or lateral sides of the body.

The image input unit 190 is for inputting a video signal and may include a camera 191 and a light emitting unit 192. The camera 191 is provided to process image frames, such as still images or moving images, obtained by the image sensor in the photographing mode. The processed image frames are transmitted to an external device/terminal through a transmission unit 155. The external device can be, for example, a computer terminal, or a mobile terminal such as a mobile phone, a smart phone, a laptop computer, a digital broadcasting terminal, a PDA (Personal Digital Assistants), a PMP (Portable Multimedia Player), and a navigation system. The external terminal can also be a fixed terminal such as a digital TV, a desktop computer, or the like.

The light emitting unit 192 is provided so as to illuminate light toward the subject when the subject is photographed. An interface unit 195 is provided on one side of the lower body portion. The interface unit 195 serves as a path for communication with all the external devices connected to the device 100. The interface unit 195 receives data from an external device, or receives power and delivers to each component of the beauty care device, and transfers the image frames or data to an external terminal connected to the device 100.

Figure 6:
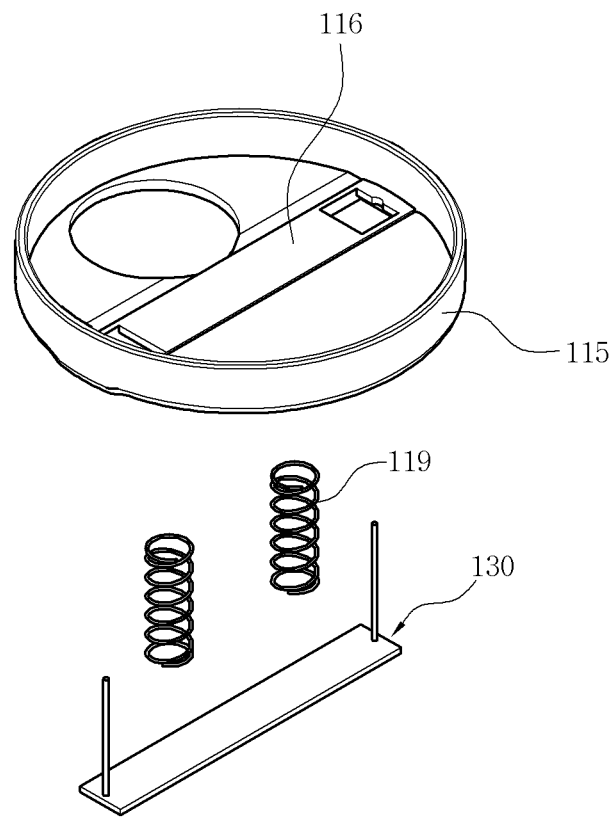
FIG. 6 is a view showing an engaging portion and an electrode unit according to the first embodiment.

Referring to FIG. 3 and FIG. 4, the case constituting the external appearance of the bodies 110 and 120 may include a front case 112, a rear case 113, and electrode cases 115, 215, and 315 (as shown in FIG. 6, 8, 11 for reference). The electrode case (115, 215, 315) may include a coupling portion for coupling the electrode unit with the body.

Various parts are embedded in the space formed between the front case 112 and the rear case 113. The cases may be formed by injection molding with a synthetic resin or may include a metal material such as stainless steel (STS) or titanium (Ti).

Referring to FIG. 3 to FIG. 5, a battery 160, an AC generator 170, a controller 151, and an auxiliary lamp 180 are received in the space between the front case 112 and the rear case 113.

Battery 160 may be a rechargeable battery such as a lithium-polymer battery. The battery 160 is disposed in a space formed between the front case 112 and the rear case 113, and is capable of supplying DC power to the AC generating member 170.

The AC generator 170 can change the DC voltage to a high-voltage AC voltage. The AC generator 170 may include an inverter. The frequency of the alternating voltage may be from a few kHz to a few hundred kHz. The peak-to-peak ac voltage may be between 3 kV and 8 kV. The output waveform of the AC generator 170 may be a sinusoidal waveform. The AC generator 170 can output a high-voltage AC pulse at a pulse frequency of several Hz to several kHz. Specifically, the driving frequency of the AC generator 170 may range from several kHz to tens of kHz. The alternating current generating member 170 can operate in a pulse mode at a pulse frequency of several Hz to several hundred Hz. A stable dielectric barrier discharge can be performed at the pulse frequency and the driving frequency.

The control unit 151 controls the overall operation of the device 100. For example, the control unit 151 may control the duty ratio of pulses of the AC generator 170 and the output of the AC generator 170. Also, the control unit 151 operates by input of the operation unit 140 and can display the operation state of the device 100 on a display unit (not shown). The control unit 151 can also control the auxiliary lamp 180. The control unit 151 can be implemented using at least one of processors, controllers, micro-controllers, and microprocessors mounted on the circuit board 150, and other electronic units for performing and controlling various functions of the device.

The auxiliary lamp 180 may be disposed between the front case 112 and the rear case 113, or may be placed while being exposed to an external area of the front or rear cases 112, 113. The on/off operation of the auxiliary lamp 180 is controlled by the controller 151, and it may be in the form of an ultraviolet LED or an infrared LED. The auxiliary lamp 180 may be turned on in synchronization with the plasma generation of the device.

The battery 160 may be embedded in the bodies 110 and 120 or may be detachably attached to the bodies 110 and 120. It may be rechargeable lithium-polymer battery. The battery 160 may be disposed in a storage space of the housing. For replacement of the battery 160, the housing body parts and the coupling part may be designed to be disassembled and recoupled with each other. The battery 160 may supply DC power to the AC generator 170.

The AC generator 170 can change the DC voltage to a high-voltage AC voltage. The AC generator 170 may include an inverter. The frequency of the alternating voltage may be several kHz to several hundred kHz. The peak-to-peak ac voltage may be between 3 kV and 8 kV. The output waveform of the AC generator 170 may be a sinusoidal waveform. The AC generator 170 can output a high-voltage AC pulse at a pulse frequency of several Hz to several kHz. Specifically, the driving frequency of the AC generator 170 may range from several kHz to tens of kHz. The alternating current generating member 170 can operate in a pulse mode at a pulse frequency of several Hz to several hundreds Hz. A stable dielectric barrier discharge can be performed at this pulse frequency and driving frequency.

The power source to be applied to the electrode unit can control the discharge on-off time of the plasma by using PWM type pulses. The generation amount of ions can be controlled according to the control of the on and off times of the plasma, and the surface temperature can also be controlled according to the plasma discharge control, and as a result, the damage of the electrode unit and the skin can effectively be avoided. However, if the conventional CW (Continue Wave) pulses are used, the surface temperature cannot be controlled effectively, and the plasma can damage and burn the skin during the operation. In addition, the oxidation of the electrode can be accelerated, and this may cause an arc discharge due to damage of the electrode surface, reducing the life of the plasma device.

The controller 151 controls the duty ratio of pulses of the AC generator 170 and controls the output of the AC generator 170. In addition, the control unit 151 may be operated by a switch, and may display the operation state on the display unit 123.

The transmitting unit 155 may be implemented through the interface unit 195 to be connected to the terminal by wire, or may be formed with a wireless communication module to be connected to the terminal wirelessly. The wireless communication module can be implemented using at least one of processors, controllers, micro-controllers, microprocessors, and other electronic units for performing various functions, that are preferably mounted on the circuit board 150.

As a wireless communication module, a module for wireless Internet access or a module for short-range communication may be used. Wireless Internet technologies, such as WLAN (Wi-Fi), Wibro (Wireless broadband), Wimax (World Interoperability for Microwave Access), HSDPA (High Speed Downlink Packet Access), can be used. Here, the short-range communication module is a module adapted for short-range communication. Bluetooth, Radio Frequency Identification (RFID), infrared data association (IrDA), Ultra Wideband (UWB), ZigBee, and the like can be used as a short range communication technology.

The user can photograph his/her skin through the video input unit 190 and transmit the image data using the transmission unit 155 mounted in the body unit, and verify or confirm the skin condition through the external terminal. The terminal can analyze the photographed image and provide information such as skin whitening and wrinkle improvement to the user.

Meanwhile, a proximity sensor may be installed on one side of the body unit on which the image input unit 190 is provided. The proximity sensor refers to a sensor that detects the presence or absence of an object approaching a predetermined detection surface or in the vicinity thereof without mechanical contact, using the force of the electromagnetic field or infrared rays. Proximity sensors have a longer lifetime and higher utilization than contact sensors.

Examples of the proximity sensor include a transmission type photoelectric sensor, a direct reflection type photoelectric sensor, a mirror reflection type photoelectric sensor, a high frequency oscillation type proximity sensor, a capacitive proximity sensor, a magnetic proximity sensor, and an infrared proximity sensor. The proximity sensor can control the operation of the camera 191 based on the sensed information. For example, when the camera 191 is moved away from the skin, the operation of the camera 191 can be turned off.

Figure 7:
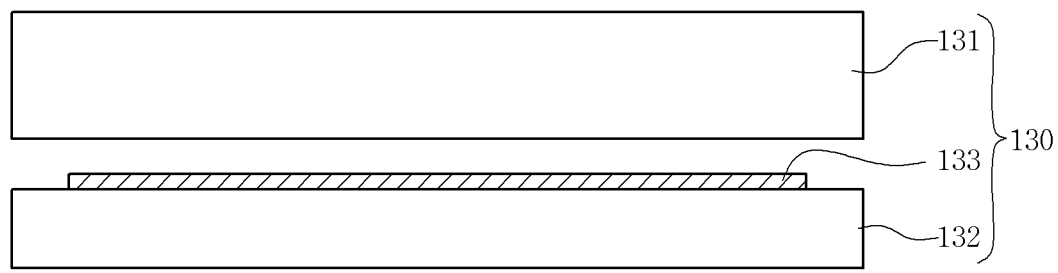
FIG. 7 is a sectional view of the electrode unit according to the first embodiment.

FIG. 6 is a view showing the engaging portion and the electrode unit according to the first embodiment, and FIG. 7 is a sectional view of the electrode unit according to the first embodiment.

Referring to FIG. 6 and FIG. 7, the electrode case 115 is detachably coupled to the rear case 113. For this, a guide protrusion is formed on the inner circumference of the electrode case 115, and a guide may be formed on the outer circumference of the rear case 113. Thus, the electrode case 115 is screwed or fitted to the rear case 113.

The electrode unit 130 according to the first embodiment has a plate shape in which a plurality of dielectric members overlap with each other. The electrode unit 130 is detachably mounted on the recessed portion 116 from one surface of the electrode case 115. The electrode unit 130 forms atmospheric plasma by the applied electric power. The electrode unit 130 may include a first dielectric member 131, a second dielectric member 132, and a conductive electrode 133 to generate a dielectric barrier discharge for the atmospheric plasma. Any one of the dielectric members may be exposed towards the skin. The conductive electrode 133 may be affixed on one surface of the dielectric member.

The thickness of the first dielectric member 131 may range from a few hundred micrometers to several millimeters. The first dielectric member 131 may have a sufficient thickness to suppress an abnormal discharge. The material of the first dielectric member 131 may be ceramic or silicon. The material of the second dielectric 132 member may be ceramic or silicon. The thickness of the conductive electrode 133 may be several micrometers to several hundreds of micrometers. The material of the conductive electrode 133 may be gold, silver, copper, or a molybdenum-manganese alloy. The conductive electrode 133 may be formed of a conductive material after being thermally processed in the second dielectric member 132. Preferably, the thickness of the conductive electrode 133 may be 10 to 15 micrometers. The conductive electrode 133 may be formed in a thin conductive pattern or in a thin plate shape.

The electrode case 115 is provided with a mounting portion 116 recessed from one surface thereof. An elastic body 119 is provided between the mounting portions 116 of the electrode unit 130. Thus, the electrode part 130 vibrates at the time of discharge, and radicals can be emitted to the surroundings. The elastic body 119 may be, for example, a coil-shaped spring, but may be a plate-like spring. Also, the electrode unit 130 itself may be made of a member having an elastic property.

Figure 8:
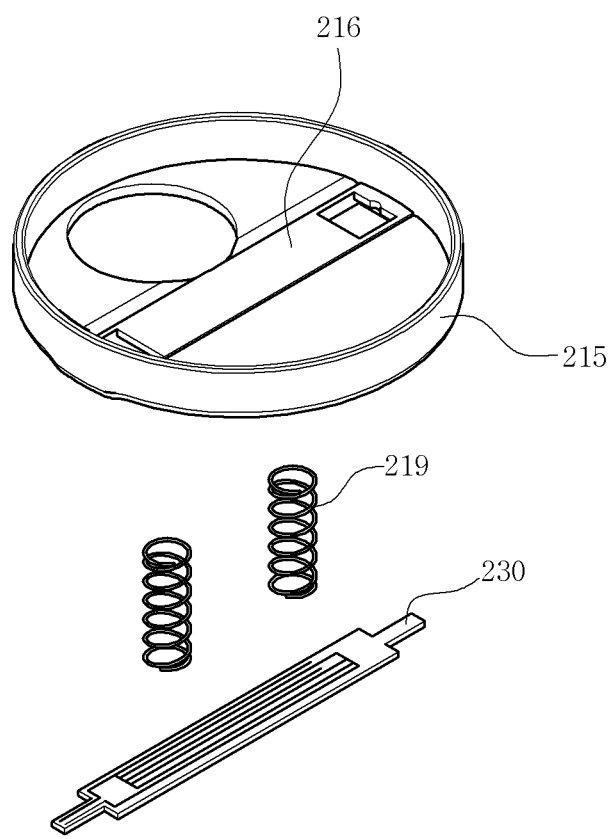
FIG. 8 is a view showing an engaging portion and an electrode unit according to a second embodiment of the present invention.
Figure 9:
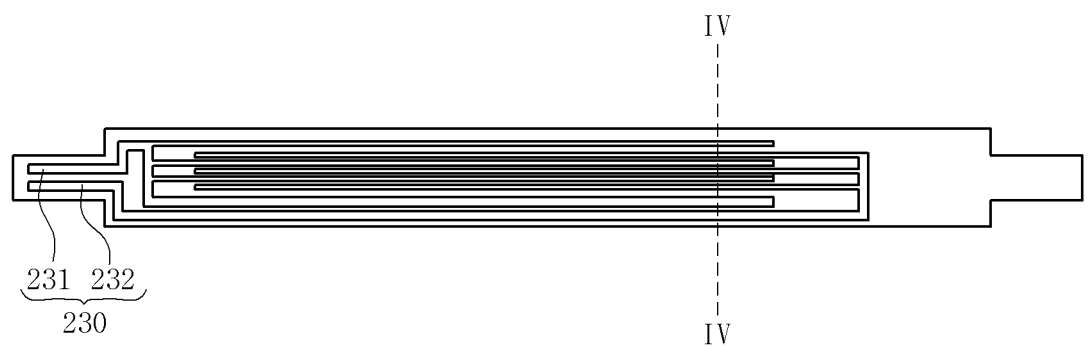
FIG. 9 is a plan view of the electrode unit according to the second embodiment.
Figure 10:
FIG. 10 is a cross-sectional view taken along the line IV-IV in FIG. 9.

FIG. 8 is a view showing an engaging portion and an electrode unit according to the second embodiment. FIG. 9 is a plan view of the electrode unit according to the second embodiment, and FIG. 10 is a cross-sectional view taken along the line IV-IV in FIG. 9.

The electrode case 215 is detachably coupled to the rear case 113. For this, a guide protrusion is formed on the inner circumference of the electrode case 215, and a guide may be formed on the outer circumference of the rear case 113. Thus, the electrode case 215 is screwed or fitted to the rear case 113.

The electrode unit 230 according to the second embodiment is formed in a thin plate shape. The electrode unit 230 is detachably mounted to the recessed portion 216 from one surface of the electrode case 215. The electrode unit 230 forms atmospheric plasma by the applied electric power. The electrode unit 230 may include a first conductor 231 and a second conductor 232 to generate a dielectric barrier discharge for atmospheric plasma. The electrode unit 230 is formed by stacking at least three films, and a first conductor 231 is formed between the first film 233 and the second film 234, and a second conductor 232 is formed between the second film 234 and the third film 235. The film may be a polyimide film. The electrode unit 230 may be formed of FPCB (FLEXIBLE PRINTED CIRCUIT BOARD).

The electrode unit 230 can have a wide band shape elongated in the longitudinal direction to generate plasma at a larger area. The first conductor 231 and the second conductor 232 are spaced apart from each other so as not to be laminated when projected on one surface. Also, at least one of the first conductor 231 and the second conductor 232 has at least three conductive lines that are divided in branches. With this configuration, a dielectric barrier discharge occurs between the conductive lines facing each other. As a result, plasma can be efficiently generated in a wider area.

The first conductor 231 and the second conductor 232 is made of a conductive material, for example, such as copper. The positive power of the alternating current generator 170 can be applied to the first conductor 231, and the negative power of the alternating current generator 170 can be applied to the second conductor 232. Also, a high-voltage alternating current pulse may be applied between the first conductor 231 and the second conductor 232. Accordingly, a dielectric barrier discharge can be generated between the first conductor 231 and the second conductor 232. The plasma generation region can be formed at a location where the discharge gap is maintained at an optimum distance between the first conductor 231 and the second conductor 232.

The first conductor 231 and the second conductor 232 may be exposed at one side of the electrode unit 230 and connected to the circuit board 150. One of the conductors can be connected to the first or second ground formed on the bodies 110 and 120 and the other can be connected to the alternating current generator 170.

The electrode case 215 is provided with a mounting portion 216 recessed from one side thereof. An elastic body 219 is mounted between the mounting portions 216 and the electrode unit 230. Therefore, the electrode unit 230 vibrates during discharging, and radicals can be emitted to the surroundings. The elastic body 219 may be, for example, a coil-shaped spring, but may be a plate-shaped spring. Also, the electrode unit 230 itself may be made of a member having elasticity.

In a modification of the electrode unit according to the second embodiment, the electrode unit may include a first film, a second film, and a first conductor and a second conductor provided between the first film and the second film. The first conductor and the second conductor are spaced from each other on the same plane, and the spacing between the conductors can be from a few micrometers to a few millimeters. With this configuration, the amount of generated atmospheric plasma ions can be controlled according to the interval.

Figure 11:
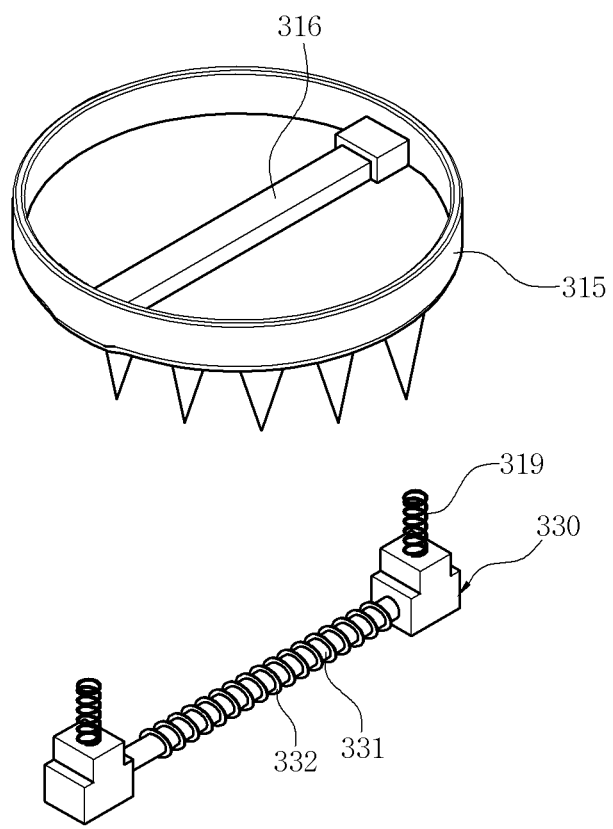
FIG. 11 is a view showing an engaging portion and an electrode unit according to a third embodiment.

FIG. 11 is a view showing an engaging portion and an electrode unit according to the third embodiment of the present invention.

The electrode case 315 is detachably coupled to the rear case 113. For this, a guide protrusion is formed on the inner circumference of the electrode case 315, and a guide may be formed on the outer circumference of the rear case 113. Thus, the electrode case 315 is screwed or fitted to the rear case 113.

The electrode unit 330 according to the third embodiment is formed such that two wires are twisted to each other. The electrode unit 330 is detachably mounted to the mounting portion 316 recessed from one surface of the electrode case 315. The electrode unit 330 forms atmospheric plasma by the applied electric power. The electrode unit 330 may include a first conductive unit 331 and a second conductive unit 332 to generate a dielectric barrier discharge for atmospheric pressure plasma.

Electrodes 330 may include the first conductive unit 331 of wire shape extending in a first direction, and the second conductive portion 332 surrounding the first conductive unit 331 and having wire-shaped and twisted to form a plurality of turns.

At least one of the first conductive unit 331 and the second conductive unit 332 may include an insulating coating layer. The first conductive unit 331 and the second conductive unit 332 are closely disposed, and a dielectric barrier discharge may be generated between the first conductive unit 331 and the second conductive unit 332.

One of the conductive unit s may be connected to the alternating current generating member 170 and the other may be electrically connected to the ground.

Each of the first conductive unit 331 and the second conductive unit 332 may include an insulating coating. The first conductive unit 331 may include a conductive wire and an insulating sheath, and the second conductive portion 332 may include a conductive wire and an insulating sheath.

The insulating sheath may be 20 micrometers to 200 micrometers thick. The thickness of the insulating coating is preferably thin. However, if the thickness of the insulating coating is too thin, a dielectric breakdown may occur.

The diameter of the first conductive part 331 and the second conductive part 332 may be 0.5 mm to 2 mm. The thickness of the first conductive part 331 may be selected according to the degree of providing flexibility. When the first conductive portion 331 and the second conductive portion 332 are twisted together, the diameter of the first conductive portion 331 and the second conductive portion 332 may preferably be the same. The material of the conductive part may be copper, and the insulating coating may be enamel.

For the dielectric barrier discharge, one of the first conductive portion 331 or the second conductive portion 332 is coated with an insulating coating. Alternatively, both of the first conductive portion 331 and the second conductive portion 332 can be coated with an insulating coating. In this case, the dielectric constant is increased and a stable discharge of plasma can be induced.

The first conductive portion 331 is connected to the AC generating member 170 and the second conductive portion 332 is grounded. In the dielectric barrier discharge, the conductive units use twisted conductive wires that are in close contact with each other in order to keep the interval between the electrodes constant. Accordingly, the dielectric discharge electrode can be easily formed without a separate patterning step.

The first and second conductive parts 331 and 332 may be twisted to each other in a helical shape. The first conductive portion 331 may be applied to the positive voltage of the alternating current generating member 170 and the second conductive portion 332 may be applied to the negative voltage of the alternating current generating member 170. A high voltage alternating current pulse can be applied between the first conductive portion 331 and the second conductive portion 332. Accordingly, a dielectric barrier discharge can be generated between the first conductive portion 331 and the second conductive portion 332. The plasma generation region can be formed at a location that maintains an optimum discharge interval on the axis of symmetry of the conductive portion. The conductive portions that are twisted with each other can apply a high electric field, relative to the planar electrodes arranged on the same plane. Thus, the start voltage of discharge can be reduced. Further, since the conductive portion uses a flexible conductive wire, it can be deformed into various shapes, and can be manufactured easily and cost can be saved.

The electrode case 315 is formed with a mounting portion 316 recessed from one surface thereof. An elastic body 319 is provided between the electrode unit 330 and the mounting portion 316. As a result, the electrode unit 330 is vibrated at the time of discharge, and radicals can be emitted to the surroundings. The elastic body 319 may be, for example, a coil-shaped spring, but may be a plate-shaped spring. Also, the electrode unit 330 itself may be made of a member having elasticity.

Figure 12:
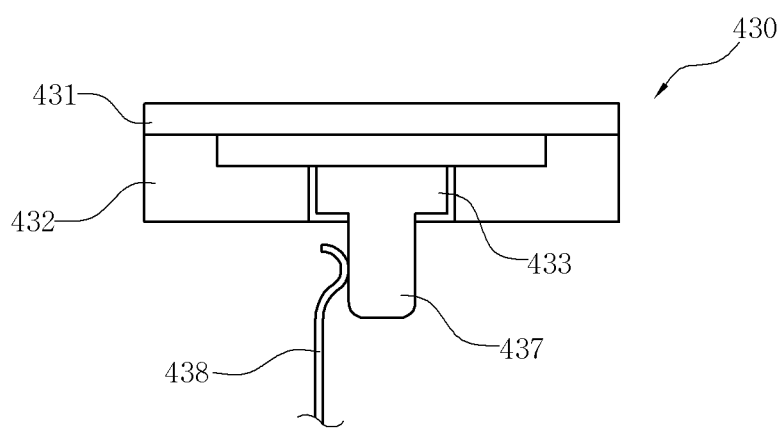
FIG. 12 is a view showing an electrode section according to a fourth embodiment.

FIG. 12 is a view showing an electrode section according to a fourth embodiment.

Referring to FIG. 12, the electrode unit 430 forming the atmospheric plasma may include a first dielectric member 431, a second dielectric member 432, and a conductive electrode 433. At this time, the conductive electrode 433 is connected to the conductive pin 437, and the conductive pin 437 is connected to the tension terminal 438 again. One end of the tension terminal 438 may be connected to the conductive pin 437 and the other end may be connected to the alternating current generating unit built in the body.

In order to compare the performance of the conventional skin modifying agent according to the embodiment of the present invention with that of the conventional skin modifying agent, a skin whitening and wrinkle reducing performance were evaluated after conducting clinical experiments on experimental group A and experimental group B as shown in the following table.

TABLE 1

|  | Group A | Group B |
|---|---|---|
| Whitening effect | 22.69% improvement | 3.26% improvement |
| Wrinkle reducing effect | 44.24% improvement | 12.24% improvement |

The above Table 1 shows the experiment results that twenty women aged 35 and over were selected for each experiment for 6 weeks.

Experimental group A was massaged for 10 minutes by pushing outward from the inside of the face for 10 minutes using the beauty care device 100 according to the first embodiment, after cleansing every evening for 6 weeks during the test period. After that, 'Aloe Vera Soothing Gel' was evenly spread and absorbed. Experimental group B was soaked in an equal amount of the same Aloe Vera soothing gel in the same area as experimental group A, every evening after cleansing for 6 weeks.

During the experiment period, the use of functional cosmetics or beauty equipment, which may affect the results of the experiment other than the above-mentioned experiment products, was totally prohibited, and neither packs nor massages were applied.

The whitening effect was measured by using a spectrophotometer, and the average value was measured three times in succession at the same position and with the uniform illumination. Accordingly, the skin tones of 20 women were measured and the average value was calculated. The wrinkle reducing effect was measured using "PRIMOS Lite", using the result of 3D matching after three consecutive shots of the right eye wrinkle using the test equipment, and finally calculating the average value after the skin tones of 20 women were measured.

As shown in Table 1, it was confirmed that the skin whitening effect and the wrinkle reducing effect were improved by using the beauty care device 100 according to the embodiment of the present invention which increases skin penetration effect of skin improving agent as compared with that using only the conventional skin-improving agent for supplying nutrition and moisture to the skin.

The above-described plasma-based beauty care device is not limited in the configurations and methods of the above-described embodiments. Various modifications can be made by using the above embodiments by selectively combining all or a part of such embodiments.

The device for use in beauty care according to the disclosed embodiments of the present invention can be used for the manufacture of various beauty care devices for reducing wrinkles, improving the skin elasticity, and enhancing other beneficial effects.

What is claimed is:

1. A skin treatment device for application of plasma to a skin, the device comprising:
   a body having a handle on which a ground is provided;
   an electrode unit mounted on one side of the body and generating an atmospheric pressure plasma by application of electric power;
   an image input unit mounted in the body and comprising a camera to capture an image of the skin; and
   a transmitting unit coupled to a controller to transmit a video signal input from the image input unit to a terminal connected to the beauty care device,
   wherein the electrode unit comprises a first film, a second film, and a third film laminated together, and a first conductor disposed between the first and second films, and a second conductor disposed between the second and third films, such that a dielectric barrier discharge is generated between the first and the second conductors,
   wherein the first conductor and the second conductor are spaced apart from each other so as not to be laminated when projected on one surface thereof,
   wherein at least one of the first and second conductors include at least three or more conductive lines that are divided in branches.

2. The skin treatment device according to claim 1,
   wherein the ground comprises a first and a second ground,
   wherein the first and second grounds are provided on two opposite sides of the body, respectively,
   wherein the electrode unit is detachably attached to a mounting portion recessed from one surface of the body.

3. The skin treatment device according to claim 2, wherein the electrode unit is electrically connected to one of the first and second grounds.

4. The skin treatment device according to claim 3, wherein the image input unit comprises:
   a light emitting unit provided on one side of the body adjacent to the camera, and
   wherein the camera is configured to capture an image of a facing skin through a hole formed on a surface of the body.

5. The skin treatment device according to claim 4, wherein the transmitting unit provided with a wireless communication module.

6. The skin treatment device according to claim 1,
   wherein the electrode unit is detachably mounted on a mounting portion recessed from one surface of the body,
   wherein an elastic body is provided between the electrode unit and the mounting portion and configured to discharge radicals generated by vibrating the electrode unit during the application of plasma.

7. A skin treatment device for application of plasma to a skin, the device comprising:
   a body having a handle on which a ground is provided;
   an electrode unit mounted on one side of the body and generating an atmospheric pressure plasma by application of electric power;
   an image input unit mounted in the body and comprising a camera to capture an image of the skin; and
   a transmitting unit coupled to a controller to transmit a video signal input from the image input unit to a terminal connected to the beauty care device,
   wherein the electrode unit comprises a first conductive unit in the form of a wire, a second conductive unit surrounding the first conductive unit and twisted to form a plurality of turns, and an insulating sheath formed on at least one of the first and second conductive units so as to generate a dielectric barrier discharge.

8. The skin treatment device according to claim 7,
   wherein the ground comprises a first and a second ground,
   wherein the first and second grounds are provided on two opposite sides of the body, respectively,
   wherein the electrode unit is detachably attached to a mounting portion recessed from one surface of the body.

9. The skin treatment device according to claim 8, wherein the electrode unit is electrically connected to one of the first and second grounds.

10. The skin treatment device according to claim 7, wherein the transmitting unit is provided with a wireless communication module.

11. The skin treatment device according to claim 7,
    wherein the electrode unit is detachably mounted on a mounting portion recessed from one surface of the body,
    wherein an elastic body is provided between the electrode unit and the mounting portion and configured to discharge radicals generated by vibrating the electrode unit during the application of plasma.

* * * * *